US006261825B1

(12) United States Patent
Hanson et al.

(10) Patent No.: US 6,261,825 B1
(45) Date of Patent: Jul. 17, 2001

(54) PRODUCTION OF AMINO ACIDS USING AUXOTROPHIC MUTANTS OF METHYLOTROPHIC BACILLUS

(75) Inventors: Richard S. Hanson, Wayzata; Michael C. Flickinger, St. Paul; Frederick J. Schendel, Falcon Heights; Michael V. Guettler, Waconia, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 07/673,264

(22) Filed: Mar. 20, 1991

Related U.S. Application Data

(63) Continuation of application No. 07/335,691, filed on Apr. 10, 1989, now abandoned.

(51) Int. Cl.[7] .............................. C12N 1/20; C12N 15/01
(52) U.S. Cl. ..................... 435/252.5; 435/832; 435/106; 435/115; 435/441; 435/446
(58) Field of Search .............................. 435/252.5, 252.1, 435/172.1, 832, 106, 115, 441, 446

(56) References Cited

U.S. PATENT DOCUMENTS

| | | | |
|---|---|---|---|
| 4,411,991 | * 10/1983 | Hirakawa et al. | .................. 435/108 |
| 4,652,527 | 3/1987 | Stirling . | |

OTHER PUBLICATIONS

Applied and Environmental Microbiology, vol. 56, No. 4, Apr. 1990, American Society for Microbiology, (Washington, DC, US), F.J. Schendel et al: "L–Lysine production at 50 degrees C. by mutants of a newly isolated and characterized methylotrophic bacillus sp.", pp. 963–970.
T. Akiba et al., *J. Ferment. Technol.*, 48, 323–328 (1970).
C. Anthony, *The Biochemistry of Methylotrophs*, Academic Press, London (1982), p. 3.
R. S. Hanson, *Adv. Appl. Microbiol.*, 26, 3–39 (1980).
A. Mimura et al., *J. Ferment. Technol.*, 56, 243–252 (1978).
R. Whittenbury et al., *J. Gen. Microbiol.*, 61, 219–226 (1970).
W. Hazeu et al., *Arch. Microbiol.*, 135, 205–210 (1983).
O. Tosaka et al., *Trends in Biotechnology*, 1, 70–80 (1983).
O. Tosaka and K. Takinami, "Lysine," in *Progress in Industrial Microbiology*, 24, K. Aida et al., eds. (1986) at 152–172.
B. Snedecor and C. L. Cooney, *Appl. Microbiol.*,27, 1112–1117 (1974).
H. J. Rogers et al., *J. Gen. Microbiol.*, 61, 155–171 (1970).
R. Doetsch, "Determinative Methods of Light Microscopy", in *Manual of Methods for General Bacteriology*, American Society for Microbiology (1981), pp. 21–33.
Laskin and Lechevalier, *CRC Handbook of Microbiology*, vol. I, CRC Press (1971), pp. 734–735.
F. W. Janssen et al., *Science*, 127, 26–27 (1958).

R. B. Cox and L. J. Zatman, *Biochem. J.*, 141, 605–608 (1974).
P. J. Large and J. R. Quayle, *Biochem. J.*, 87, 386–396 (1963).
M. Mandel and J. Marmur, *Methods Enzymol.*, 12, 195–206 (1968).
T. Gregersen, *Eur. J. Appl. Microbiol. Biotechnol.*, 5, 123–127 (1978).
E. Work, *Biochem. J.*, 67, 416–423 (1957).
A. G. Brooke et al., *Arch. Microbiol.*, 151, 268–273 (Feb. 1989).
L. Dijkhuizen et al., *FEMS Microbiol. Lett.*, 52, 209–214 (Jul. 1988).
I. Shiio, "Tryptophan, Phenylalanine and Tyrosine," 188–206 (1986).
*Program of the 88th Annual Meeting of the American Society for Microbiology*, pp. 123–124.
*Program of the 89th Annual Meeting of the American Society for Microbiology*, p. 193.
F. J. Schendel et al., "L–Lysine Production from Methanol at High Cell Densities of MGA3, a Thermophilic Bacillus," Abstract from 1989 ASM Annual Meeting (published Mar. 21, 1989).
M. Guettler and R. S. Hanson, "Characterization of a Methanol Oxidizing Thermophilic Member of the Genus Bacillus," Abstract from 1988 ASM Annual Meeting (published Mar. 16, 1988).
M. Guettler and R. S. Hanson, "Characterization of a Methanol Oxidizing Thermophilic Member of the Genus Bacillus," Poster Session Materials presented at the 88th Annual Meeting of the American Society for Microbiology, Wednesday, May 11, 1988.
Gerhardt et al. "Manual of Methods for General Bacteriology" 1981, pp. 230–231.*
Clement et.al., Abstract 3–24, 5th Int. Symp. of Microbial Growth on C1 compounds, Groningen, Aug. 1986.*
Tanaka, et al., Bull. Inst. Chem. Res., Kyoto Univ. (1975), 53(3), 284–314.*
Shiio et al., "Effect of Biotin on the Bacterial Formation of Glutamic Acid", *The Journal of Biochemistry*, vol. 51, No. 1, pp. 56–62 (1962).
Shiio et al., "Cellular Permeability and Extracellular Formation of Glutamic Acid in *Brevibacterium flavum*", *The Journal of Biochemistry*, vol. 53, No. 5, pp. 333–340 (1963).
Takinami et al., "Biochemical Effects of Fatty Acid and its Derivatives on L–Glutamic Acid Fermentation", *Agr. Biol. Chem.*, vol. 28, No. 2, pp. 114–119 (1964).

(List continued on next page.)

Primary Examiner—Irene Marx
(74) Attorney, Agent, or Firm—Merchant & Gould P.C.

(57) ABSTRACT

A method of producing amino acids by culturing an amino acid auxotroph of a biologically pure strain of a type I methylotrophic bacterium of the genus Bacillus which exhibits sustained growth at 50° C. using methanol as a carbon and energy source and requiring vitamin $B_{12}$ and biotin is provided.

16 Claims, 6 Drawing Sheets

OTHER PUBLICATIONS

Nara et al., "Effect of Penicillin on Amino Acid Fermentation", *Agr. Biol. Chem*, vol. 28, No. 2, pp. 120–124 (1964).

Snedecor et al., "Thermophilic Mixed Culture of Bacteria Utlilizing Methanol for Growth", *Applied Microbiology*, vol. 27, No. 6, pp. 1112–1117 (1974).

Hazeu, et al., "Norcardia sp. 239, a facultative methanol utilizer with the ribulose monophosphate pathway of formaldehyde fixation", *Arch. Microbiol*, vol. 135, pp. 205–210 (1983).

Simon, et al., "A Broad Host Range Mobilization System For In Vivo Genetic Engineering: Transposon Mutagenesis In Gram Negative Bacteria", *Bio/Technology*, pp. 784–791 (Nov. 1983).

Brooke et al., "Environmental control of metabolic fluxes in thermotolerant methylotrophic Bacillus strains", *Arch Mirobiol* vol. 151, pp. 268–273 (1989).

Ha et al., *PNAS*, 85:8017 (1988).

Berg et al., *Biotechnology*, 1(5):417 (1983).

Lamb et al., *PNAS*, 86:7890 (1989).

Tosaka et al., "Process Spotlight: The production of L–lysine by fermentation", *Trends in Biotechnology*, vol. 1, No. 3, pp. 70–73 (1983).

\* cited by examiner

PRODUCTION OF AMINO ACIDS USING AUXOTROPHIC MUTANTS OF METHYLOTROPHIC BACILLUS

This is a continuation, of application Ser. No. 07/335,691, filed Apr. 10, 1989 now abandoned.

SUPPORT

This invention was made with Government support under Contract Number DE-ACO2-82ER12029, awarded by the United States Department of Energy. The Government has certain rights in the invention.

BACKGROUND OF THE INVENTION

This invention relates to production of amino acids using auxotrophic mutants of a methylotrophic Bacillus.

Microorganisms that utilize one-carbon compounds more reduced than carbon dioxide (methylotrophs) are diverse and ubiquitous. Anthony, The Biochemistry of methylotrophs, p 3 (Academic Press, London 1982); Hanson, *Adv. Appl. Microbiol.*, 26:3 (1980). Those methylotrophic bacteria reported to utilize methane are all gram-negative and nearly all have an obligate requirement for one-carbon compounds as energy sources (Anthony, supra; Whittenburg et al. *J Gen. Microbiol.* 61: 219–226 (1970)). Bacteria that grow on methanol and methylamines but not methane include several facultative as well as obligate methylotrophs (Anthony, supra; Hanson, supra. All the obligate methylotrophs unable to utilize methane are gram-negative aerobic bacteria (Anthony, supra.; Whittenburg, supra). Of the facultative methylotrophs isolated that utilize methanol, methylamine or both, only a few were gram positive and were assigned to the genera Bacillus, Corynebacterium, Arthrobacter, or Nocardia (Akiba et al, *J. Ferment. Technol.*, 48:323–328 (1970); Clement et al. *Abstracts of the Fifth International Symposium Microbiol. Growth on $C_1$Compounds*, p. 69 (Free Univ. Press, Amsterdam 1986); Hazen et al, *Arch. Microbiol.*, 135: 205–210 (1983); Mimura et al., *J. Ferment. Technol.*, 56: 243–252 (1978).

Production of single cell protein and selected amino acids by microbial fermentation is known, e.g., U.S. Pat. No. 4,652,527 to Stirling. One amino acid which has been produced on an industrial scale is lysine, see Tosaka et al., *Trends in Biotechnology*, 1: 70–74 (1983), Tosaka and Takinami, *Progress in Industrial Microbiology*, Ch. 24, p. 152–172 (Aida et al., 1986). Bacillus species have been used in fermentation processes to produce amino acids, Tosaka et al., supra.; Tosaka and Takinami, supra. However, to date no production of amino acids using an isolated Bacillus species capable of rapid growth on methanol at temperatures above 50° C. has occurred.

The industrial advantages of a thermophilic methanol utilizing fermentation process at elevated temperatures have been described, Snedecor and Cooney, *Appl. Microbiol.*, 27: 112–1117 (1974). For example, use of elevated temperatures can significantly reduce cooling costs. A methanol utilizing, thermophilic mixed culture that included an endosporeforming species was selected by Snedecor and Cooney; however, Snedecor and Cooney, were unable to isolate a pure culture capable of growth on methanol. It is extremely difficult or impossible to isolate appropriate mutants from mixed or impure cultures.

Accordingly, there is a need for a method of producing amino acids using a type I methylotrophic bacterium of the genus Bacillus which exhibits sustained growth at 50° C. in medium having a nitrogen source, vitamin $B_{12}$ and methanol as a source of carbon and energy.

SUMMARY OF THE INVENTION

We have discovered a biologically pure strain of a type I methylotrophic bacterium of the genus Bacillus which exhibits sustained growth at 50° C. in nutrient media comprising methanol as a source of carbon and energy, vitamin $B_{12}$ and biotin. The bacterium grows at temperatures from about 45° C. to about 55° C. and contains a soluble $NAD^+$ dependent alcohol dehydrogenase.

We have further discovered that amino acid auxotrophs of the biologically pure strain mentioned above are useful for producing substantial amounts of amino acids. In a preferred embodiment, an amino acid auxotroph of the biologically pure strain type I methylotrophic bacteria of the genus Bacillus produces at least one amino acid when cultured at 50° C. in an aqueous nutrient media having a carbon and energy source, preferably methanol, a nitrogen source, vitamin $B_{12}$, and biotin.

In a further preferred embodiment the bacterium of the present invention is capable of simultaneous production of multiple amino acids useful as animal feeds and animal feed supplements or as nutritional supplements for animal feeds. The amino acid(s) produced according to the present invention can be subsequently separated from the culture media. Preferably, the culture media containing the amino acids can be dried and used directly as a valuable animal feed or animal feed supplement.

A preferred auxotrophic bacterium of the present invention is a mutant of biologically pure strain MGA3 and morphological variants thereof. Most preferably, the amino acid auxotrophs of the present invention are also resistant to amino acid analogues.

A preferred nutrient media for culturing the bacterium of the present invention to produce amino acids includes a carbon and energy source, preferably methanol a nitrogen source, vitamin $B_{12}$, and biotin together with effective amounts of a phosphate source, a sulfate source, a calcium source and trace elements. Amino acid production by auxotrophic bacterium of the present invention is enhanced by automatically feeding the culture media with effective amounts of methanol and trace elements together with required amino acids. lost preferably amino acid production is maximized when cells grow to high cell density by using a continuous culture process including effective amounts of methanol, trace elements and required amino acids. In preferred, semi-continuous (fed batch) or continuous culture methods, production of amino acids is non-growth associated at constant cell density.

We have observed that using the method of the present invention, auxotrophic bacteria of a biologically pure strain of type I methylotrophic Bacillus excrete substantial amounts of lysine. In a preferred embodiment we have observed an amino acid auxotroph excreting from about 3–10 grams/per liter L-lysine. A more preferred auxotrophic mutant for use in production of lysine is a homoserine auxotroph that is resistant to growth inhibition by S-2-aminoethyl-cysteine and analogs of threonine and methionine. A most preferred auxotroph, is a homoserine auxotroph that is resistant to inhibition by S-2-aminoethyl-cysteine and is also a mutant requiring phenylalanine and tyrosine which is resistant to tryptophan, tyrosine and phenylalanine analogs.

The present invention also is directed to a method of obtaining amino acid producing mutants of a biologically pure strain of a type I methylotrophic bacterium of the genus Bacillus involving the steps of isolating a biologically pure strain of a type I methylotrophic bacterium of the genus Bacillus that exhibits sustained growth at 50° C. in an aqueous nutrient media comprising a carbon and energy source, preferably methanol, vitamin $B_{12}$ and biotin and treating the isolated bacterium with an amount of mutagenic agent effective to produce a mutant exhibiting increased amino acid production. Amino acid producing mutants are selected based on the ability to grown on media containing one or more desired amino acids or biosynthetic intermediates. In a preferred embodiment, isolated type I methylotrophic Bacillus of the present invention are treated with either or both a chemical mutagen such as ethyl methane sulfonate or N-methyl-N-nitro-N'-nitrosoguanine or an amino acid analog such as S-2-aminoethyl-L-cysteine to increase amino acid production by the bacterium.

Other features and advantages of the invention will be apparent from the following detailed description and appended claims.

DETAILED DESCRIPTION OF THE INVENTION

The methylotrophic bacterium of a preferred embodiment of the present invention is a member of the genus Bacillus having the characteristics as set forth in Table I, below.

TABLE 1

Characteristics of Type I Methylotrophic Bacillus

| | |
|---|---|
| Cell shape | rod |
| Gram-reaction | + |
| Endospores | oval |
| Sporangia | swollen |
| Spore localization | subterminal |
| Survival after 10 min at 80° C. | + |
| Sporulation at 53° C. | – |
| Sporulation at 37° C. | + |
| Optimum pH for growth | 7 |
| Optimum temperature for growth | 45–55° C. |
| Vitamin requirements | $B_{12}$, Biotin |
| Carbon and energy sources: | |
| Methanol | ++ |
| Mannitol | ++ |
| Glucose | + |
| Ribose | w |
| Maltose | w |
| Acetate | w |
| Glutamate | w |

TABLE 1-continued

Characteristics of Type I Methylotrophic Bacillus

| | |
|---|---|
| α-Ketoglutarate | w |
| Gas from carbohydrate | – |
| Growth on nutrient agar | w |
| Nitrogen Source: | |
| Ammonium | + |
| Nitrate | – |
| Nitrate reduction | – |
| Nitrate respiration | – |
| Urease | + |
| Catalase | – |
| Hexulose phosphate synthase | + |
| Hydrolysis of: | |
| Gelatin | + |
| Starch | + |
| NaCl tolerance | 1% |
| DNA base ratios (moles % G + C) | 44 |

Footnotes: w = weak positive; . = not determined.

Figure 1:
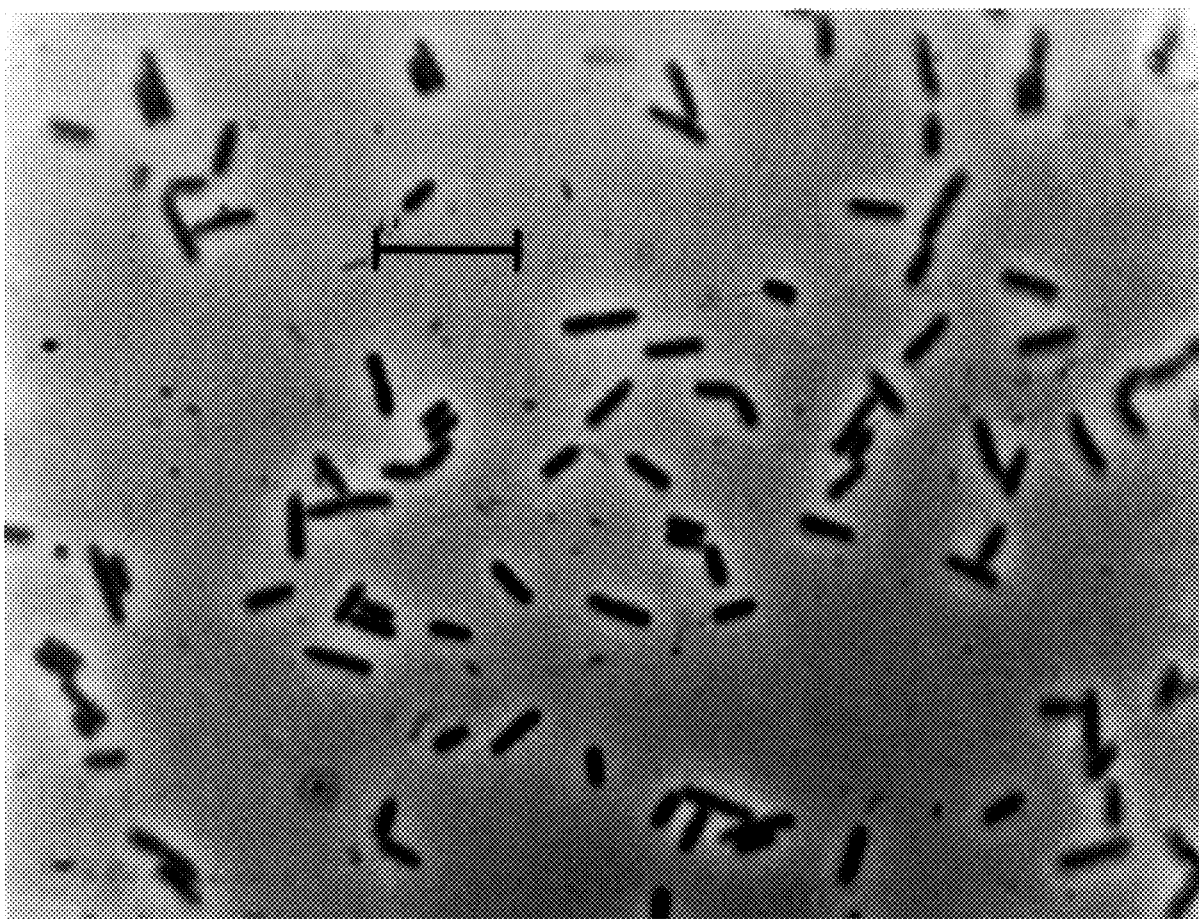
FIG. 1 is a phase contrast photomicrograph of strain MGA3 grown on MV medium at 53° C. The bar indicates 10 μm.
Figure 2:
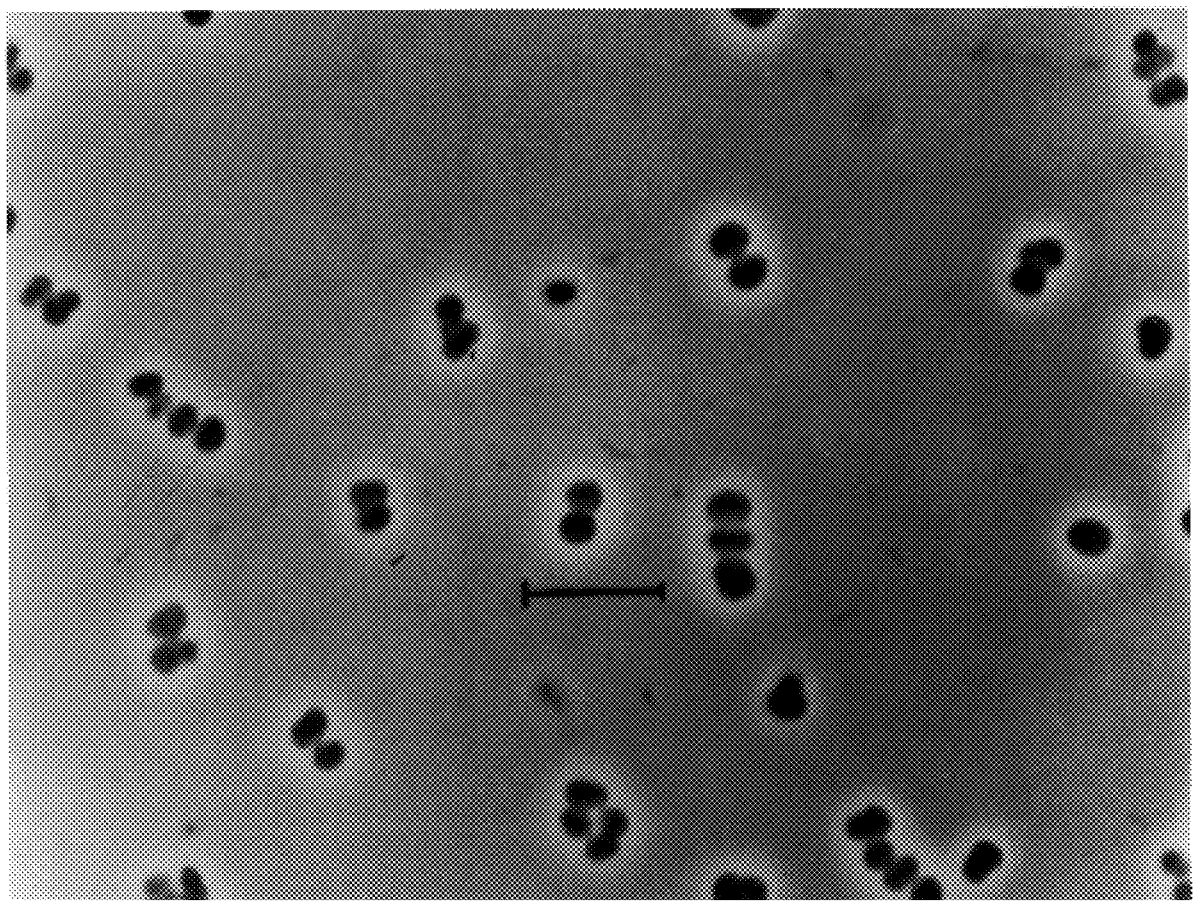
FIG. 2 is a phase contrast micrograph of strain Gr grown on MV medium at 45° C.

Bacillus strain MGA3 isolated in the manner described herein exhibited the characteristics indicated in Table I—(FIG. 1). Bacillus stain MGA3 has been deposited with the American Type Culture Collection 12301 Parklawn Drive, Rockville, Md. and has been assigned number ATCC No. 53907. *Bacillus methanolicus* NOA2 was deposited on Jun. 3, 1999 and received Patent Deposit Designation PTA-166. The Depository is American Type Culture Collection, 10801 University Boulevard, Manassas, Va. 20110-2209. The bacterium is further characterized by an aberrant form in which very large and pleomorphic cells were occasionally visible in smears of strain MGA3 cultures that were reminiscent of the pleomorphic cells seen in an original fermentor enrichment. A colony from a plate of MGA3 produced a pure culture of this morphological variant (FIG. 2). It was designated strain Gr. This strain shared most of the cultural and physiological characteristics of strain MGA3 that were tested. Strain Gr grew on methanol or mannitol at 50° C., was neutrophilic, and required vitamin $B_{12}$ and biotin for growth, and resembled strain MGA3 in all other characteristics tested (Table 1). Crude extracts of strain Gr also contained hexulose-phosphate-synthase activity. Strain Gr formed phase bright spores when a culture was switched from the nonpermissive 53° C. to 37° C. A culture of strain Gr grown at high temperature did not survive heat inactivation but cells from a culture incubated an additional 18 hours at 37° C. survived 80° C. for 10 minutes. The gross appearance of Gr was similar to the rod mutants of *Bacillus subtilis* and *Bacillus licheniformis* isolated by Rogers et al., *J. Gen. Microbiol.* 61:155–171 (1970).

Primary characteristics of the bacterium of the present invention are that it grows at a temperature of at least 50° C. in an aqueous nutrient media that includes methanol as a sole carbon and energy source with biotin, and vitamin $B_{12}$ as a required vitamins. As described herein "aqueous nutrient media" refers to a water based composition including minerals and their salts necessary for growth of the bacterium of the present invention. Preferred nutrient media contains an effective amount of a phosphate source, a nitrogen source, a sulfate source, calcium and trace elements. As described herein "trace elements" refers to elements essential for growth in trace concentrations i.e., minute fractions of 1 percent (1000 ppm or less). As indicated in Table 1, the bacterium of the present invention can utilize a number of carbon and energy sources for growth other than methanol; including glucose or mannitol; however the preferred carbon and energy source is methanol.

A satisfactory media for the present invention is a minimal salts media, such as that described in Example 1 or the like. In a preferred embodiment, such as Example 1, minimal salts media to grow the bacterium of the present invention includes from about 20 to about 500 mM ammonium sulfate; from about 10 to 125 mM potassium phosphate, from about 0.1–1.5 mM calcium chloride; and salts of magnesium, and the trace metals: iron, copper, manganese, zinc, molybdenum, borate and cobalt in concentrations as stated in Example 4. The amount of methanol and vitamin $B_{12}$ needed for growth can vary. The amount of methanol in the media can range from about 0.05% wt/vol. to about 5% wt/vol., with amounts of from about 0.2% wt/vol. to about 0.5% wt/vol. preferred. The media should contain at least 0.05% wt/vol. methanol. The amount of vitamin $B_{12}$ in the aqueous media can range from about 0.5 $\mu g \cdot l^{-1}$ to 1 $mg \cdot l^{-1}$, with amounts from about 1 $\mu g \cdot l^{-1}$ to 0.1 $mg \cdot l^{-1}$ preferred. Optimal growth of the bacterium takes place at 45–55° C. within a pH range of about 6.0–8.0. No growth occurs at 65° C. or when the pH is 5.5. Growth requires biotin in amounts from about 20 $\mu g \cdot l^{-1}$ to 20 $mg \cdot l^{-1}$. When grown in minimal salts media with methanol, vitamin $B_{12}$ and biotin the bacterium of the present invention can grow at a rate from about 0.2 $hr^{-1}$ to about 1.5 $hr^{-1}$. at a temperature of about 50° C. to 60° C.

The type I methylotrophic bacterium of the present invention further produces a NAD+ dependent methanol dehydrogenase. This dehydrogenase has optimal activity at 65° C. when isolated from the organism of the present invention and is believed to be useful for inclusion in methanol sensing electrodes, production of $NADH+H^+$ from an inexpensive electron donor and for driving other enzyme coupled reactions requiring a reductant.

The bacterium of the present invention is characterized by its ability to form auxotrophs capable of producing amino acids and morphological mutants such as strain Gr. The bacterium also produces endospores at 37° C. and not above about 50° C. which is important to strain preservation. As defined herein "auxotroph" refers to an organism requiring specific growth factors in addition to the carbon source present in a minimal nutrient media. With respect to the present invention auxotroph refers to mutagenized forms of the type I methylotrophic bacterium described herein which require one or more amino acids for growth and overproduce and excrete one or more amino acids. As defined herein "mutation" in general refers to a sudden heritable change in the phenotype of an organism which can be spontaneous or induced by known mutagenic agents, including radiation and various chemicals. Auxotrophs of the present invention can be produced using a variety of mutagenic agents including radiation such as ultra-violet light, and x-rays and chemical mutagens. Examples of chemical mutagens are ethyl methane sulfonate (EMS), N-methyl-N-nitro-N'-nitrosoguanine (NTG) and nitrous acid.

The present invention is also directed to production of amino acid analog resistant strains of the type I methylotrophic bacterium described herein that overproduce and excrete various amino acids. As defined herein "amino acid analog" refers to a compound structurally similar to an amino acid but which does not react with the biosynthetic enzymes and genetic control elements in the same way as the natural amino acid. Examples of such structurally similar analogs and their related amino acid are 5-methyl-DL-tryptophan (MT), p-fluorophenylalanine and ethionine, 5-fluoro-DL-tryptophan (FT) and S-2-aminoethyl-L-cysteine (AEC); which correspond to tryptophan, tyrosine, tryptophan, lysine, and methionine respectively.

As described in the Examples, amino acid producing mutants of type I methylotrophic bacterium of the present invention are produced by treating the isolated type I methylotrophic bacterium described herein with an amount of mutagenic agent effective to produce mutants that overproduce one or more amino acid. While the type and amount of mutagenic agent to be used can vary use of EMS and NTG in amounts from about 10 and 50 $\mu g \cdot ml^{-1}$, respectively is preferred. After mutagenic treatment, isolates of the treated bacterium are tested for growth on media containing at least vitamin $B_{12}$ and biotin and one or more amino acids. One suitable medium to select amino acid excreting mutants is minimal vitamin media of the type described in Example 1 or the like. Auxotrophic isolates are identified by their ability to grow only on minimal vitamin media containing one or more specific amino acids. Numerous amino acids auxotrophs of the present invention are identified in Example 2.

The type I methylotrophic bacterium described herein can also be treated alternatively or additionally with an amino acid analog to select for mutants which overproduce specific amino acids. In one preferred embodiment, amino acid producing mutants are first treated with the chemical mutagenic agent EMS (10 $\mu g \cdot ml^{-1}$ or NTG (50 $\mu g \cdot ml^{-1}$) to produce amino acid auxotrophs. Chosen amino acid auxotrophs are then treated with increasing amounts of the amino acid analog AEC to select for mutants that overproduce the amino acid lysine. It is envisioned that the present invention can be employed to produce amino acid auxotrophs and/or amino acid analog resistant mutants of the type I methylotrophic bacterium of the genus Bacillus described herein that are capable of producing most, if not all, of the known amino acids.

To produce amino acids from auxotrophic and/or amino acid resistant mutants of the type I methylotrophic Bacillus of the present invention, the organism is cultured in an aqueous nutrient medium having biotin, vitamin $B_{12}$, and methanol together with amounts of a phosphate source, a sulfate source, a nitrogen source, calcium and trace elements in amounts such as indicated in Example 4. As previously described a satisfactory media is a minimal salts media, such as described in Example 1 or the like. The amounts of methanol and vitamin $B_{12}$ needed for production of amino acids can vary. Methanol can range from about 0.05% wt/vol. to 5% wt/vol. with an amount of from about 0.3% to about 0.8% wt/vol. methanol preferred. Vitamin $B_{12}$ can range from about 0.5 $\mu g \cdot l^{-1}$ to 1 $mg \cdot l^{-1}$. With amounts of about 1 $\mu g \cdot l^{-1}$ to about 0.1 $\mu mg \cdot l^{-1}$ preferred. At a minimum, at least about 0.05% wt/vol. methanol, 0.5 $\mu g \cdot l^{-1}$ vitamin $B_{12}$ and about 20 $\mu g \cdot l^{-1}$ to about 20 $mg \cdot l^{-1}$ biotin are needed for mutant production of amino acids.

In a preferred embodiment, phosphate, magnesium and calcium are fed to the media coupled to pH control with ammonium hydroxide. Many nitrogen sources can be used such as ammonium chloride, ammonium sulfate and ammonium nitrate. The preferred nitrogen sources are ammonium chloride or $(NH_4)_2SO_4$ required in amounts of at least 20 mmoles.

If desired, the amino acid produced in the culture can be separated using known extraction procedures such as ion exchange chromatography. In a preferred method the fermentation broth including the type I methylotrophic Bacillus, culture media components and amino acids produced is dried directly to produce a material containing cells, media components and one or more over produced essential amino acids which are useful as an animal feed or animal feed supplement. The fermentation broth can be dried by, for example, the method reported in G. L. Solomons, "Materials and Methods in Fermentation:, (Academic Press, N.Y. N.Y. 1964).

Employing auxotrophs and/or amino acid resistant mutants of the type I methylotrophic bacterium of the present invention it is believed that amino acids can be produced in substantial quantities. That is, quantities of amino acids from at least 5 grams·$l^{-1}$ to about/50 grams·$l^{-1}$ preferably from about 50 grams·$l^{-1}$ to about 150 grams and more preferably from about 100 to 150 g·$l^{-1}$ can be produced. While the present invention is believed useful to produce many of the 20 amino acids, it is especially useful to produce lysine, phenylalanine, and tryptophan either singly or simultaneously. In one embodiment, auxotrophs which are also amino acid sensitive can produce from about 3 to about 5 g·$l^{-1}$ of lysine. In a preferred embodiment, auxotrophs which are also amino acid senstive can produce up to 8 grams/l L-lysine. Simultaneous production of at least 4.0 g·$l^{-1}$ of L-lysine and at least 1.5 g·$l^{-1}$ of L-aspartic acid can also be obtained. In one preferred embodiment, simultaneous production of 4.5 g·$l^{-1}$ of L-lysine and 2.0 g·$l^{-1}$ of L-aspartic acid are obtained.

When cultivated on minimal salts media of the type described in Example 1 type I methylotrophic strains of the present invention can grow at cell densities up to 50 grams·$l^{-1}$ dry wt. Preferably, cell growth on minimal salts media with vitamin $B_{12}$, biotin and methanol at temperatures between 45° C. and 55° C. can be at least 150 g·$l^{-1}$ (dry weight) and up to 0.6 grams cells per gram methanol. Cell densities of 30–50g·$l^{-1}$ (dry weight) with cell yields of about 0.53 grams cells per gram methanol have been observed.

Auxotrophs of the present invention can produce amino acids when grown in batch culture. However, fed-batch or semi-continuous feed of methanol and trace elements with required amino acids enhances amino acid production. Amino acid production by auxotrophs of the present invention can be further enhanced by using continuous culture methods in which trace elements are automatically fed with required amino acids. Further, phosphate, magnesium and calcium feeding to a batch-fed or continuous culture can be coupled to pH control. Production of amino acids by auxotrophs is maximized when the bacterium of the present invention is grown to the highest cell densities by using continuous addition of methanol, and trace elements to culture media together with continuous addition of pure oxygen.

EXAMPLE 1

ISOLATION AND CHARACTERIZATION OF STRAIN MGA3

A. Methods and Procedures

Growth and Sporulation Media: Minimal salts medium (MS) contained in one liter of distilled water: $K_2HPO_4$, 3.8g; $NaH_2PO_4.H_2O$, 2.8g; $(NH_4)_2SO_4$, 3.6g; $MgSO_4.7 H_2O$, 0.5g; $FeSO_4.7 H_2O$, 2 mg; $CuSO_4.5 H_2O$, 40 $\mu$g; $H_3BO_3$; 30 $\mu$g; $MnSO_4.4 H_2O$, 200 $\mu$g; $ZnSO_4.7 H_2O$, 200 $\mu$g; $Na_2MoO_4$, 40 $\mu$g; $CaCl_2.2 H_2O$, 5.3 $\mu$g; $CoCl_2.6 H_2O$, 40 $\mu$g. The pH of this medium was adjusted to 7.0 prior to autoclaving. The phosphates were reduced by 50% when MS medium was used for continuous cultures.

The minimal vitamin medium (MV) was MS medium supplemented with thiamine-HCl, D-calcium pantothenate, riboflavin, and nicotinamide, each at 50 $\mu$g·$l^{-1}$, biotin and folic acid, each at 20 $\mu$g·$l^{-1}$ and $B_{12}$ at 1 $\mu$g·$l^{-1}$.

Yeast extract medium (MY) was MS medium supplemented with yeast extract 0.5 g·$l^{-1}$.

All media (MV and MY) contained 0.4% (vol/vol) methanol unless otherwise stated. Nutrient broth (NB) contained beef extract 3 g and peptone 5 g in 1000 ml distilled water. J vitamin medium (JV) contained tryptone (5g) and yeast extract (15 g) per liter and the vitamins at the same concentration as MV medium. Sporulation medium (SM) was composed of three parts NB and four parts MV medium. All solid media was prepared by combining double strength medium components with an equal amount of 3% bacto agar after autoclaving.

Enrichment: Freshwater marsh soil was suspended in distilled water and heated for 20 minutes at 90° C. A portion of this suspension was used as an inoculum for the fermentors operating as batch cultures at 53° C. When growth was apparent in the vessels, the medium pumps were turned on and the flow rate was gradually increased to produce continuous cultures for enrichment.

Continuous Cultures: Two 1-liter Omni-Culture fermentors (The Virtis Company, Gardiner, N.Y.) were used for continuous cultures. A metering pump (Ismatec Mini, Chicago, Ill., S-820) fed an unsterilized MS medium into the vessels and flow was adjusted between 0.1 and 0.5 volumes per hour. A separate metering pump fed methanol at a rate that maintained a residual concentration of approximately 2 g·$l^{-1}$ in the out-flow. The concentration of methanol was measured by gas chromatography. The pH was automatically controlled at pH 6.8 by the addition of 10% v/v ammonium hydroxide (Controller Model 5656-00, Cole Parmer Instrument Co., Chicago, Ill.). The temperature was maintained between 53° C. and 56° C. Air was sparged at 2 v/v/m and three flat blade turbine impellers were operated at 600 RPM.

Isolation of Pure Cultures: Samples from the fermentors were periodically streaked on MY and MV agar and incubated at 53° C. Isolated colonies that were obtained from these plates were restreaked and grown under the same conditions. Colonies were tested for growth on methanol by inoculating 2 ml of MV medium into 18 mm tubes and incubating the tubes in a gyratory water bath shaker at 53° C. Tubes with growth in this methanol minimal broth were streaked onto MV agar for further purification.

Morphological Characteristics: Gram strain, spore strain, and poly-β-hydroxy-butyrate straining were done as described in the Doetsch, *Manual of Methods for General Bacteriology* pp. 21–33 (American Society for Microbiology 1981). Gram strains were verified with the KOH test conducted as described by Gergersen, supra. Cell size was determined with cells grown on MY agar for 18 hours at 50° C.

Characterization Tests: The API Rapid CH and Rapid E strip systems (Sherwood Medical, Plainview, N.Y.) were used to provide a standardized fermentation study of 49 substances and nine additional biochemical determinations respectively. Cultures used to inoculate two sets of strips were grown for 18 hours at 55° C. on the JV agar medium and on SM agar medium. The test strips were inoculated and read according to the directions provided with the system. Tests for nitrate reduction, NaCl tolerance, tyrosine decomposition, and lysozyme tolerance were performed as described by Gordon et al., *The Genus Bacillus Handbook No. 427* (Washington, D.C., Dept. of Ag. 1973) but with the following changes. The reduction of nitrate to nitrite, NaCl tolerance, and lysozyme tolerance were tested in JV medium; tyrosine decomposition was tested in JV medium with tyrosine (5 g·$l^{-1}$) and 0.5% methanol. To test the suitability of nitrate as an nitrogen source, potassium nitrate (5 g·$l^{-1}$) was substituted for the ammonium sulfate in the MV medium.

Hydrolytic Activity: MV agar plates with 0.5% (vol/vol) methanol, were prepared to detect hydrolytic activity by adding soluble starch (3 g·$l^{-1}$), fruit pectin (Certo Brand, 10 g·$l^{-1}$), and gelatin (Sigma Type I, 4 g·$l^{-1}$) to MV media prior to pouring the plates. Plates containing casein were prepared with 15 g non-fat dry milk (Carnation Company) in a liter of half strength MV media. Hydrolysis on these plates was detected as described in Laskin and Lechevalier, CRC *Handbook of Microbiology*, pp. 734–735 (CRC Press, 1971).

Dipicolinic Acid Extraction and Determination: Dipicolinic acid (DPA) was extracted by autoclaving 5 ml samples of cell suspensions for 20 minutes. The samples were then cooled, acidified with 1 ml of 1N acetic acid, allowed to stand for 1 hour, and then centrifuged at 12,000×g for 10 minutes. The amounts of DPA in the supernatant fractions were determined by the colorimetric assay described by Janssen et al. *Science* 127:26–27 (1958). Sporangia and cell counts were determined visually with the use of a Petroff-Hauser counting chamber.

Heat and Chloroform Resistance: A portion of culture was heated to 80° C. and then maintained at 80° C. for 10 minutes. Viable and heat stable counts were determined by plating appropriate dilutions of the heated and unheated culture on MY agar. The plates were incubated at 45° C. for 48 hours before the colonies were counted. A spore suspension was prepared from a culture grown at 50° C. for 18 hours and at 37° C. for 18 hours in MY. The culture was centrifuged at 12,000 g, washed, in distilled water by centrifugation and resuspended in distilled water. The spore suspension was pasteurized at 65° C. for 10 minutes. A portion of this suspension was then heated at 80° C. for 10 minutes. Spore counts were determined by plating dilutions on MV agar and incubating the plates at 50° C. for 48 hours.

Chloroform, 5 μl, was added to test tubes (13 mm×100 mm) containing 1 ml of a culture. After mixing the suspension on a vortex mixer, the tube was incubated at 37° C. for 10 minutes prior to dilution and plating as described above.

Growth Experiments: The growth responses to various substrates were determined in MV medium containing alcohols, at 0.5% (vol/vol); sugars, organic acids and methyl substituted amines, each at 0.3% (wt/vol); and formaldehyde, at 0.03% (wt/vol). The effects of pH on growth were determined in MV medium with the pH adjusted by addition of HCl or NaOH. Growth rates were determined by growth of culture in triple baffled flasks (Bellco Model 2540) on a gyratory shaker (New Brunswick Model G-7) operated at approximately 200 RPM. Growth was measured by turbidimetric measurements at 650 nm using a spectrophotometer or Klett units (#66 filter), using a Klett Summerson colorimeter. One absorbance unit was equivalent to 0.42 $g \cdot l^{-1}$ of dry cell weight.

Antibiotic Susceptibility: An 0.2 ml volume of a mid-exponential phase culture was spread onto MV agar plates containing 0.5% vol/vol methanol. The plates were incubated for 1 hour at 55° C. to dry the surface. Antibiotic containing discs (Difco Laboratories, Detroit, Mich.) were then aseptically placed on the surface and the plates were returned to 55° C. for 48 hours. The antibiotic discs used to test susceptibility contained gentamicin 10 mcg, sulfadiazine 300 mcg, tetracycline 30 mcg, ampicillin 10 mcg, rifampin 5 mcg, chloromycetin 30 mcg, erythromycin 5 mcg, and penicillin G 10 units.

Methanol Oxidation: Cultures of Bacillus strain MGA3 were grown to mid-exponential phase in liquid MV media with methanol ($4 g \cdot l^{-1}$) or mannitol ($3 g \cdot l^{-1}$) at 50° C. Cells were harvested at 4° C. by centrifugation at 12,000×g for 8 minutes, washed by centrifugation in ice cold 0.05 M phosphate buffer pH 7.0 and suspended in ice cold 0.05 M phosphate buffer. Methanol oxidation was measured using a Rauk oxygen electrode (Rauk Bros., Bottisham, England).

Oxygen consumption was measured by placing a suspension of cells (3.7–7.3 $mg \cdot ml^{-1}$) in 0.05 M phosphate buffer in the electrode. After the rate of endogenous oxygen consumption was established, methanol 1.0 $g \cdot l^{-1}$ was added to the electrode and the rate of methanol dependent oxygen consumption was measured.

Crude Extracts and Enzyme Assays: Cells were harvested in mid-exponential phase, resuspended in 50 mM phosphate buffer, pH and disrupted by two passages through a French pressure cell operated at 15,000 psi. The cell debris was separated by centrifugation at 12,100 g and the supernatant fraction was used as the crude extract. Hexulose phosphate synthase was assayed by the method of Cox and Zatmann; *Biochem J.*, 141:605–608 (1974), incorporated by reference herein and hydroxypyruvate reductase was assayed by the method of Large and Quayle *Biochem J.*, 87:387 (1963) incorporated by reference herein. Protein concentrations were determined with Biuret reagent by the method of Clark and Switzer *Experimental biochemistry* (2nd ed. Freeman Press 1977), incorporated by reference herein. Bovine serum albumin was employed as a standard.

DNA Base Composition:

The DNA base composition was determined by measuring the hyperchromic shift in absorbance as a function of temperature in 0.12 M sodium phosphate pH 6.8 with *E. coli* DNA as a standard, Mandel and Marmur, *Methods Enzymol.*, 12:195–206 (1968).

B. RESULTS

Enrichment and Isolation: Development of a methanol-utilizing mixed culture at 53–56° C. was rapid and abundant. When a continuous culture was established, dilution rates could be raised to 0.45 per hour without washout. Smears revealed a preponderance of Gram positive forms including spore-forming bacteria, and a variety of morphological types including some very large pleomorphic cells. However, only bacteria that did not grow when returned to methanol minimal medium could be readily isolated from the enrichment vessels. After screening many isolates, (using the isolation procedure described above one was found that grew rapidly in MV medium at 53° C. and was given the strain designation MGA3.

Cell and Colony Morphology: Cells of strain MGA3 were rod shaped (0.8–1.0 by 2.5–4.5 μm) with rounded ends (FIG. 1). Young cultures stained Gram positive and all cultures were KOH negative. V-shaped pairs of cells were frequent in cultures. Vacuoles were never seen and poly-β-hydroxybutyrate was not detected by Sudan black B staining. Colonies produced on MV agar were colorless, translucent, circular, convex, and had entire margins. Streak cultivation produced colonies of various sizes and all colonies grew larger on MV agar supplemented with amino acids, glucose, yeast extract, or small amounts of nutrient broth than on unsupplemented MV agar. Pigments were not produced.

Figure 3:
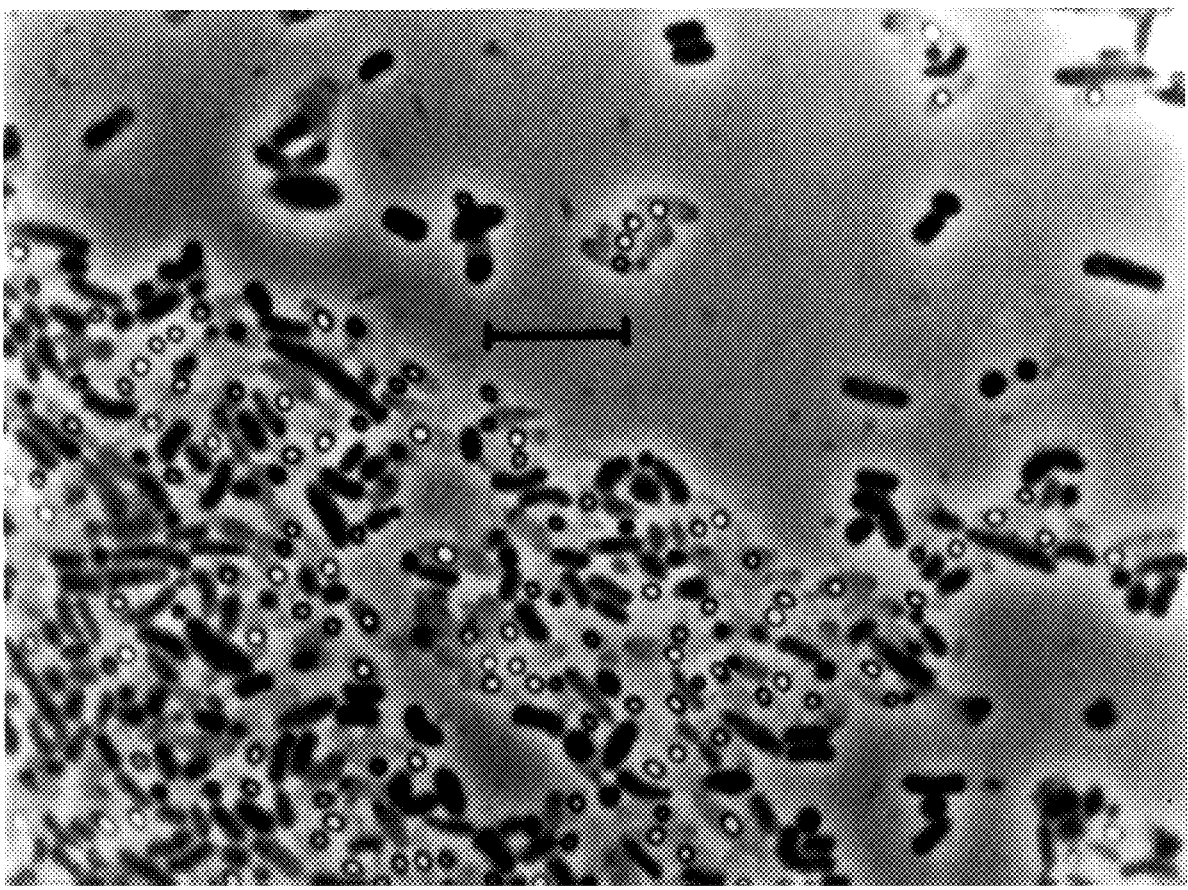
FIG. 3 is a phase contrast photomicrograph of strain MGA3 grown on SM medium at 53° C. and shifted to 37° C. The bar represents 10 μm.

Endospores: Spores were oval and 0.8–1.0 by 1.1–1.2 μm, their location was subterminal and sporangia were swollen (FIG. 3). It was noticed that most cultures grown on MV agar at 53° C. did not contain refractile endospores and lost viability rapidly when stored at room temperature. These cultures did not grow when inoculated into fresh media. However, cultures that contained endospores produced growth in fresh media even after heating at 80° C. for 10 minutes. Strain MGA3 grew well at 50–55° C. but most cells lysed without producing endospores. It was noted that endospores were formed in cultures that were incubated at 50–55° C. for 18 hours and then incubated at 37° C. for an additional 18 hours. When cultures were grown under these conditions 54% of the cells contained refractile endospores and chloroform resistant colony forming units were equal to 10% of the viable cell counts ($2.7 \times 10^{-7}$ viable cells·ml$^{-1}$). It was also noted that supplemented methanol media (MY,SM) produced more endospores than the minimal medium (MV). Nutrient agar or nutrient agar with added manganese sulfate (5 mg·l$^{-1}$) did not serve as a good sporulation media.

Heat Tolerance: Exponential-phase cultures of MGA3 grown at 50° C. and containing $3.1 \times 10^8$ colony forming units (CFU) per ml were completely killed by heating for 10 minutes at 80° C. A pasteurized spore suspension from cultures grown 18 hours at 53° C. and incubated an additional 18 hours at 37° C. contained $7.37 \times 10^7$ CFU when plated on a methanol-salts medium (MV). The same suspension contained $3.5 \times 10^7$ CFU after heating at 80° C. for 10 minutes.

Dipicolinic Acid: Dipicolinic acid is a compound absent from vegetative bacteria but present in large amounts in endospores. A culture of *Methylophilus methylotrophus* grown in MV medium at 37° C. and a culture of strain MGA3 grown in MV at 50° C. and then switched to 37° C. were each the source of 70 mg (wet weight) of cell paste. Each cell paste was extracted and assayed for dipicolinic acid. The cells of *Methylophilus methylotrophus* contained no detectable dipicolinic acid while the cells of MGA3 contained 0.189 mg dipicolinic acid.

Growth: Strain MGA3 grew well in J medium, a complex medium used to grow fastidious species of Bacillus, Gregersen, *Eur. J. Appl. Microbiol. Biotechnol.* 5:123–123 (1978) incorporated by reference herein, and grew poorly in nutrient broth or on nutrient agar. The organism grew rapidly in MV medium that contained methanol or mannitol. Of the vitamins present in this medium, only vitamin $B_{12}$ stimulated growth and both vitamins $B_{12}$ and biotin was absolutely required for growth. Strain MGA3 grew more slowly when the medium contained glucose as the source of carbon and energy. Maltose, ribose, acetate, glutamate, and alpha-ketoglutarate were utilized poorly, and growth from galactose was scant or doubtful. Lactose, sucrose, xylose, formate, succinate, glycerol, ethanol, n-propanol, n-butanol, formaldehyde, methylamine, diethylamine, or trimethylamine were not utilized.

Acid was produced from only 7 of the 49 substrates used in the API rapid CH test (ribose, D-glucose, mannitol, maltose, D-tagatose, D-arabitol, and 5-keto-gluconate). Gas was not produced from any of the following substrates:

Glycerol, erythritol, D-arabinose, L-arabinose, D-xylose, L-xylose, adonitol, beta-methyl-xyloside, galactose, D-fructose, D-mannose, L-sorbose, rhamnose, dulcitol, inositol, sorbitol, alpha-methyl-D-mannoside, alpha-methyl-D-gluconate, N-acetyl-glucosamine, amygdalin, arbutin, esculin, salicin, cellobiose, lactose, melibiose, saccharose, trehalose, insulin, melezitose, D-raffinose, starch, glycogen, xylitol, β-gentiobiose, D-turanose, D-lyxose, D-fucose, L-fucose, L-arabitol, gluconate, or 2-keto-gluconate.

Strain MGA3 grew in JV broth that contained 1% NaCl but not in broth that contained 5% NaCl.

Growth on Methanol: Of the eight vitamin components in MV medium, only vitamins $B_{12}$ and biotin was required for growth of strain MGA3 on methanol. If vitamin $B_{12}$ is eliminated from MV medium, growth of strain MGA3 does not occur. Nitrate was not utilized as a nitrogen source.

Growth of strain MGA3 in methanol was optimal at pH 7.0–7.5. Growth did not occur at pH 5.5. The optimum growth temperature was found to be between 50° and 53° C. The organism grew in MY medium at 30 and at 61° C.; it failed to grow at 25 and 65° C.

TABLE 2

The effect of temperature on the growth rate of Bacillus Strain MGA3 in medium MV.

| Temperature Degree | $\mu$ (h$^{-1}$) |
|---|---|
| 37 | 0.24 |
| 45 | 0.41 |
| 50 | 0.51 |
| 53 | 0.43 |
| 56 | 0.38 |

Figure 4:
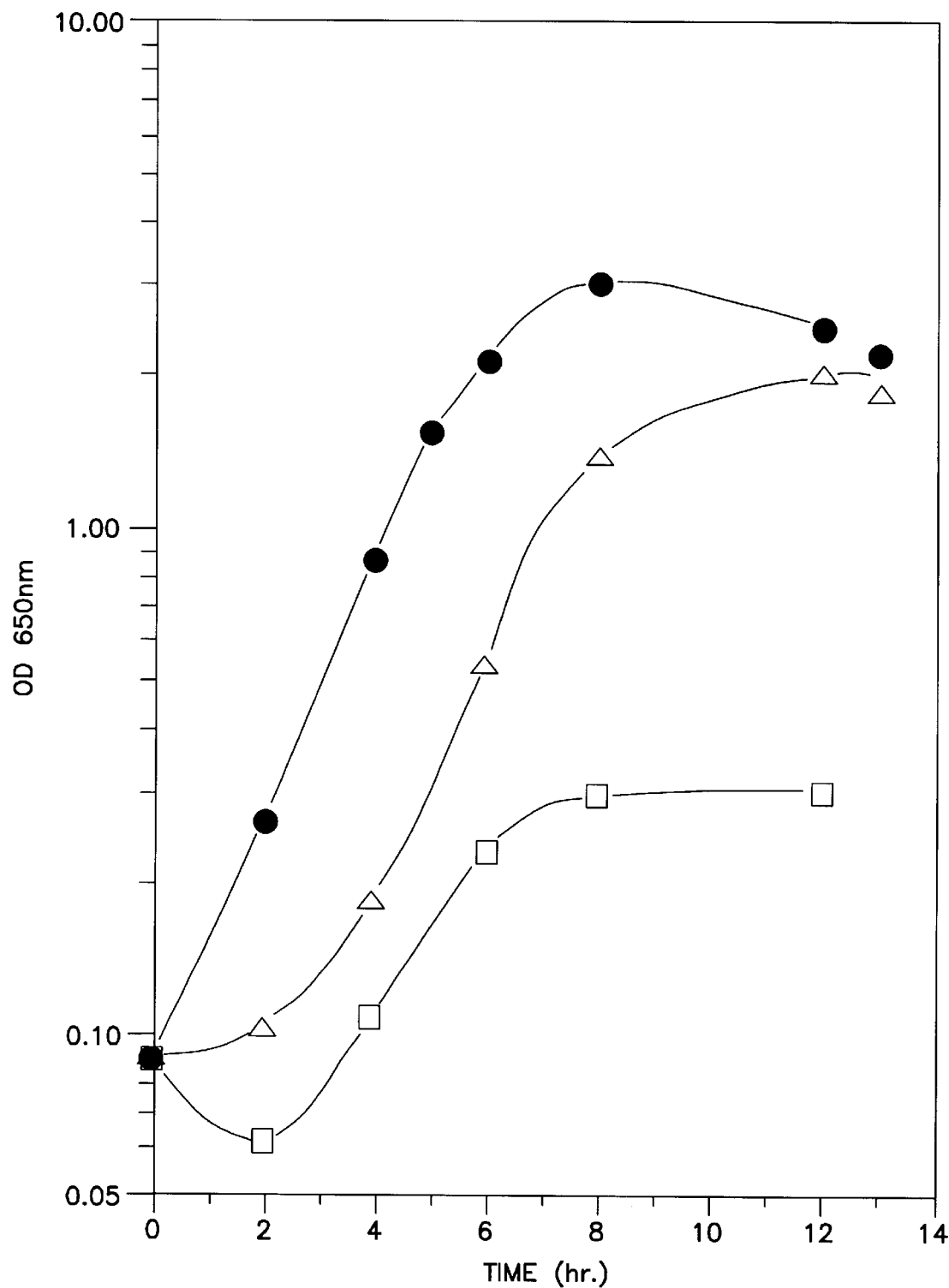
FIG. 4 shows growth of strain MGA3. Strain MGA3 was inoculated into MV media containing 0.5 g·l$^{-1}$ yeast extract (-□-), methanol 5.0 g·l$^{-1}$ (-Δ-) or methanol 5 g·l$^{-1}$ and 0.5 g·l$^{-1}$ yeast extract (-○-). The cultures were incubated with shaking at 53° C.

Strain MGA3 had a generation time of 1.4 hours in MV medium at 50° C. Growth on methanol was stimulated by the small additions of complex nutrient mixtures such as yeast extract. Generation times were reduced to approximately 1 hour in these media (FIG. 4).

Biochemical Characterization:

Crude cell extracts prepared from methanol grown cultures of MGA3 lacked hydroxypyruvate reductase activity but contained high hexulose-6-phosphate synthase activity. The specific activity of hexulose-6-phosphate synthase was 6.27–3.72 $\mu$m of formaldehyde utilized per minute per mg of protein. Strain MGA3 did not produce catalase or tyrosine-degrading enzymes. Starch, gelatin, and pectin were hydrolyzed but growth was inhibited on casein containing plates. The API Rapid E tests indicated the presence of cytochrome oxidase, urease and acetoin. The Rapid E tests for β-galactosidase, lysine decarboxylase, ornithine decarboxylase, citrate utilization, phenylalanine deamination, and indole were negative. Nitrate was not reduced to nitrite.

Methanol oxidation by cell suspensions grown with methanol or mannitol as carbon and energy sources was measured at 50° C. and 37° C. Cells grown with methanol as the carbon and energy source oxidized methanol at a rate of $5.8 \times 10^{-4}$ mMoles·min$^{-1}$·mg$^{-1}$ at 37° C. Cells grown with mannitol as the carbon and energy source oxidized methanol at a rate of $6.5 \times 10^{-5}$ mMoles·min·mg$^{-1}$ at 50° C.

Antibiotic Susceptibility: Strain MGA3 was sensitive to all antibiotics tested.

DNA Base Composition: DNA isolated from strain MGA3 had a base content of 44 moles per cent G+C.

EXAMPLE 2

A. Production of Auxotrophic Mutants

Amino acid auxotrophs and lysine producing strains were derived from two environmental isolates, Bacillus MGA3 (isolation described in Example I above) and NOA2 (isolated pursuant to procedure in Example I above but from separate source; and exhibits identical characteristics as MGA3 as described in Example I.)

The standard mutagenesis, used to derive both amino acid auxotrophs and analog resistant mutants, was a treatment with ethyl methane sulfonate (EMS) or N-methyl-N-nitro-N'-nitrosoguanine (NTG). The cells to be mutagenized were grown to late log phase (2.5 OD) in MV medium plus casamino acids (CAA 0.2%). The culture (2.5 ml) was combined with an equal amount of fresh medium and the chemical mutagen was added in the following amounts:

|     | per ml    | minutes | ° C. |
| --- | --------- | ------- | ---- |
| NTG | 50 μg     | 10–15   | 50   |
| EMS | 10–20 μl  | 20–25   | 37   |

This was followed by dilution and outgrowth in a medium containing either casamino acids (0.2–0.4%), the amino acids of interest (50 mg/l), or both. After 6 hours outgrowth, this culture was diluted with three parts carbon free medium and incubated at 37° C. for 18 hours. Spores were centrifuged, washed twice, and the spore suspensions were stored at 4° C. Appropriate dilutions of spore suspensions were plated on amino acid containing agar and incubated at 50° C. for 36 hours. Colonies were replicated to amino acid containing media and minimal media, and incubated overnight at 50° C. Colonies that appeared to require one or more amino acids for growth were tested for growth on individual amino acids and mixtures of amino acids in order to define the specific amino acid requirements. The mutagenic treatments that produced mutants important to the production lysine, tryptophan, phenylalanine and other amino acids are outlined in the following table:

Production of Auxotrophs:

| Parent | Date | Agent | Conditions conc.[1] | min. | New Mutant |
| --- | --- | --- | --- | --- | --- |
| Gr | 07/22/88 | NTG | 50 | 10 | 7/30–15(hse⁻) |
| MGA3 | 12/08/87 | EMS | 10 | 15 | S12 (hse⁻) ATTC No. 53908 |
| #55 | 07/22/88 | NTG | 50 | 10 | 10/12–11(leu⁻) 10/12–24(tyr⁻) |
| 10/12–24 (tyr⁻) | 11/01/88 | NTG | 50 | 10 | 11/25–1(tyr⁻phe⁻) 12/9–1(tyr⁻ala⁻) 11/26–1(tyr⁻trp⁻) |
| NOA2 | 08/11/88 | NTG | 50 | 10 | 8/14–4 (hse⁻) 8/16–5(hse⁻) 9/31–4(phe⁻) |
| 9/31–4 (phe⁻) | 11/01/88 | NTG | 50 | 10 | 11/10–12 (phe⁻tyr⁻) |

[1]NTG μg/ml; EMS μl/ml

B. Proof of Auxotrophy

The amino acid requirements of each auxotrophic isolate were proven by their growth response to amino acids added to MV broth medium. The following table gives references to this data for all auxotrophs that are important to the production of lysine and other amino acids.

Response to Required Amino Acids:

| Auxotroph | Genotype |
| --- | --- |
| 7/30–15 | Hse⁻ |
| 7/30–15 | Hse⁻ |
| S-12 | Hse⁻ |
| R2 | Hse⁻ |
| 10/12–11 | Leu⁻ |
| 10/12–11 | Leu⁻ |
| 10/12–24 | Tyr⁻ |
| 10/12–24 | Tyr⁻ |
| 12/9–1 | Tyr⁻Ala⁻ |
| 12/9–1 | Tyr⁻Ala⁻ |
| 12/9–1 | Tyr⁻Ala⁻ |
| 11/26–1 | Tyr⁻Trp⁻ |
| 11/26–1 | Tyr⁻Trp⁻ |

-continued

| Auxotroph | Genotype |
| --- | --- |
| 11/25–1 | Tyr⁻Phe⁻ |
| 8/14–4 | Hse⁻ |
| 8/16–5 | Hse⁻ |
| 9/31–4 | Phe⁻ |
| 11/10–12 | Phe⁻Tyr⁻ |
| 11/10–12 | Phe⁻Tyr⁻ |

EXAMPLE 3

ANALOG RESISTANCE

The lysine analog S-2-aminoethyl-L-cysteine (AEC) has been used effectively to select for lysine overproducing mutants from among auxotrophic and nonauxotrophic strains of MGA3 and NOA2. Mutants resistant to as much as 2 g/l of AEC have been produced in a stepwise manner (up to 5 steps so that AEC resistance of 2 g·l$^{-1}$ is achieved; at approximately 0.25 g·l$^{-1}$ increments) by plating mutagenized cells on MV media containing AEC and methionine, threonine, and isoleucine (250–500 mg/l). At each step media was incubated at 50° C. for 3 days. The resulting resistant isolates were challenged on media containing higher AEC concentrations until the desired level of resistance was reached or until an additional mutagenesis was required. There has been good correlation between increased AEC resistance and increased lysine production. The prototrophic strain MGA3 #55 was selected in the manner described above, was resistant to 2 g·l$^{-1}$ of AEC, and produced a 0.12 gram·l$^{-1}$ of lysine. The amount of lysine produced was improved by the introduction of auxotrophic markers unrelated to the lysine pathway, e.g., 11/25-1 (try⁻phe⁻) and 12/9-1 (tyr⁻ala⁻) which produced 0.6 and 0.8 g·l$^{-1}$ amounts of lysine respectively. Homoserine minus mutants such as 8/14-4 (hse⁻) produced about the same amount of lysine (0.6–0.9g·l$^{-1}$) even without high AEC resistance; but the amount produced could be approximately doubled by selecting for mutants resistant to higher concentrations of AEC (600–1500 mg/l).

EXAMPLE 4

LYSINE OVER PRODUCTION

Lysine was determined in culture supernatants by the acidic ninhydrin assay method, described in Work, *Biochem. J.* 67:416–423 (1957), incorporated by reference herein. The ninhydrin reagent was prepared by combining 64 ml of glacial acetic acid, 16 ml of 0.6 M phosphoric acid, and 1 g of ninhydrin (Sigma #N-4876). Culture samples were centrifuged for 2 minutes at high speed in an Epindorph centrifuge. Culture supernatant (0.05 ml) was combined with ninhydrin reagent (0.55 ml) in 5 ml screw capped Pyrex tubes. Standard solutions of lysine were treated the same way. The tubes were heated for 1 hour in a 100° C. water bath and glacial acetic acid (1.4 ml) was added to the cooled tubes. Absorbance was read at 440 nm on a Beckmann DU-70 spectrophotometer that computed the lysine concentration through regression analysis. The assay results were very linear and repeatable from day to day. Alternatively, amino acids were determined by HPLC using pre-column derivatization with o-phtalaldehyde (OPA) and fluorescence detection of the OPA-amino acid derivative. Culture supernatants were diluted 50–500 fold with methanol, and then centrifuged for 2–5 minutes at high speed to remove any precipitated protein. The sample (25 µL) was then mixed with o-phtalaldehyde (Pierce #26015) (50 µML), then injected onto a 5 µ particle size C-18 reverse phase column (Alltech #28066). Separation of the OPA amino acids was carried out using a flow rate of 1 mL/min and a non-linear gradient from 10–50% acetonitrile in 50 mM potassium phosphate (pH 6.8).

Shake Flask Screening Method

For screening of potential lysine producers, mutants of MGA3 or NOA2 were grown on medium containing 10 g/L $K_2HPO_4$, 32 g/L $(NH_4)_2SO_4$, 10 g/L $CaCO_3$, 0.2 g/L $MgCl_2.6\ H_2O$, 20 g/L methanol, trace metals at the concentration described below, vitamins (biotin, 50 µg/L and $B_{12}$ 10 µg/L), and 200 mg/L of any amino acids required for growth. The strains were cultured in 25 mL of the above medium in a 250 mL baffled shake flask covered with milk filter disks, and a piece of 2 mil teflon membrane to reduce methanol evaporation. The cultures were started using a 1–4% inoculum and grown at 50° C. in an air shaker with a revolution rate of 300 rpm. The concentration of methanol was determined every 12 hours by removing a sample, separating the cells by centrifugation, and injecting the supernatant into a gas chromatograph. More methanol was added to the flask if the concentration dropped below 200 mM. Experiments were usually carried out for a period of 24–48 hours. Lysine formation was determined by either ninhydrin or HPLC. The results from screening several mutants are shown in Table 3. These result correlated well with the production of lysine in 5 liter stirred tank reactor with a methanol feeding.

TABLE 3

| Strain | Shake Flask Lysine (g/L) | Reactor Lysine (g/L) |
| --- | --- | --- |
| NOA2 8/14–4 | 0.96 | 2.2 |
| NOA2 R2 | 0.60 | 0.50 |
| NOA2 8/16–5 #1 | 2.6 | ND[1] |
| NOA2 8/16–5 #3 | 2.8 | 4.5 |
| Gr 7/30–15 #1 | 4.1 | 4.0 |
| Gr 7/30–15 #2 | 7.0 | 7.0 |
| MGA3 11/25–1 | 0.58 | ND |
| MGA3 12/9–1 | 0.11 | 0.8 |
| NOA2 8/16–5 | 7.8 | 8.0 |

[1]ND=not determined

Lysine Production in a Stirred Reactor

Lysine was over produced in the aerated stirred reactor by culturing the appropriate mutant strain of the present invention using either sulfate or phosphate limited minimal salts media. When sulfate limitation was used, ammonium chloride replaced the ammonium sulfate, and all trace metals were used as their chloride salts. The sulfate required for growth was supplied as potassium sulfate. The amino acids required for growth of the lysine producers were supplied at the concentrations necessary to reach the desired cell densities by feeding either pure amino acids or amino acid hydrolysates. Cells can be cultured with growth rates from 0.5–1 µmax using the following concentration ranges of nutrients.: ammonium sulfate from 20–500 mM, sulfate from 0.1–500 mM, methanol from 20–800 mM, phosphate from 10–125 mM, magnesium from 0.5–20 mM, manganese from 2–100 µM, iron from 10–800 µM, calcium from 0.1–1.5 mM, chloride from 0–80 mM, zinc from 1–20 µM, cobalt from 0.1–20 µM, copper from 0.1–20 µM, molybdate from 0.2–40 µM, borate from 0.4–8 µM, vitamin $B_{12}$ from 0.5 µg·l$^{-1}$–1 mg·l$^{-1}$, and biotin from 20 µg·l$^{-1}$–20 mg·l$^{-1}$. The pH of the reactor was maintained at 7.1 by the addition of ammonium hydroxide. The dissolved oxygen concentration was maintained at a level of 10% by adjusting either the agitation rate, the aeration rate, or by the addition of pure oxygen. Foaming was controlled by the automatic addition of a silicon based antifoam (SAG-471). The methanol concentration was monitored by gas chromatography, and maintained between 50–600 mM by periodic addition of methanol to the reactor. Lysine production was primarily nongrowth associated, and excess threonine was shown to inhibit lysine formation. The amount of lysine formed was essentially the same when either phosphate or sulfate limitation was used. When the organism Gr 7/30-15 #1 was cultivated in the reactor under sulfate limitation, a total of 4.0 g·l$^{-1}$ of cell dry weight produced 7.0 g·l$^{-1}$ of lysine during the 40 hour cultivation.

EXAMPLE 5

SIMULTANEOUS OVER PRODUCTION OF MORE THAN ONE AMINO ACID

Figure 5:
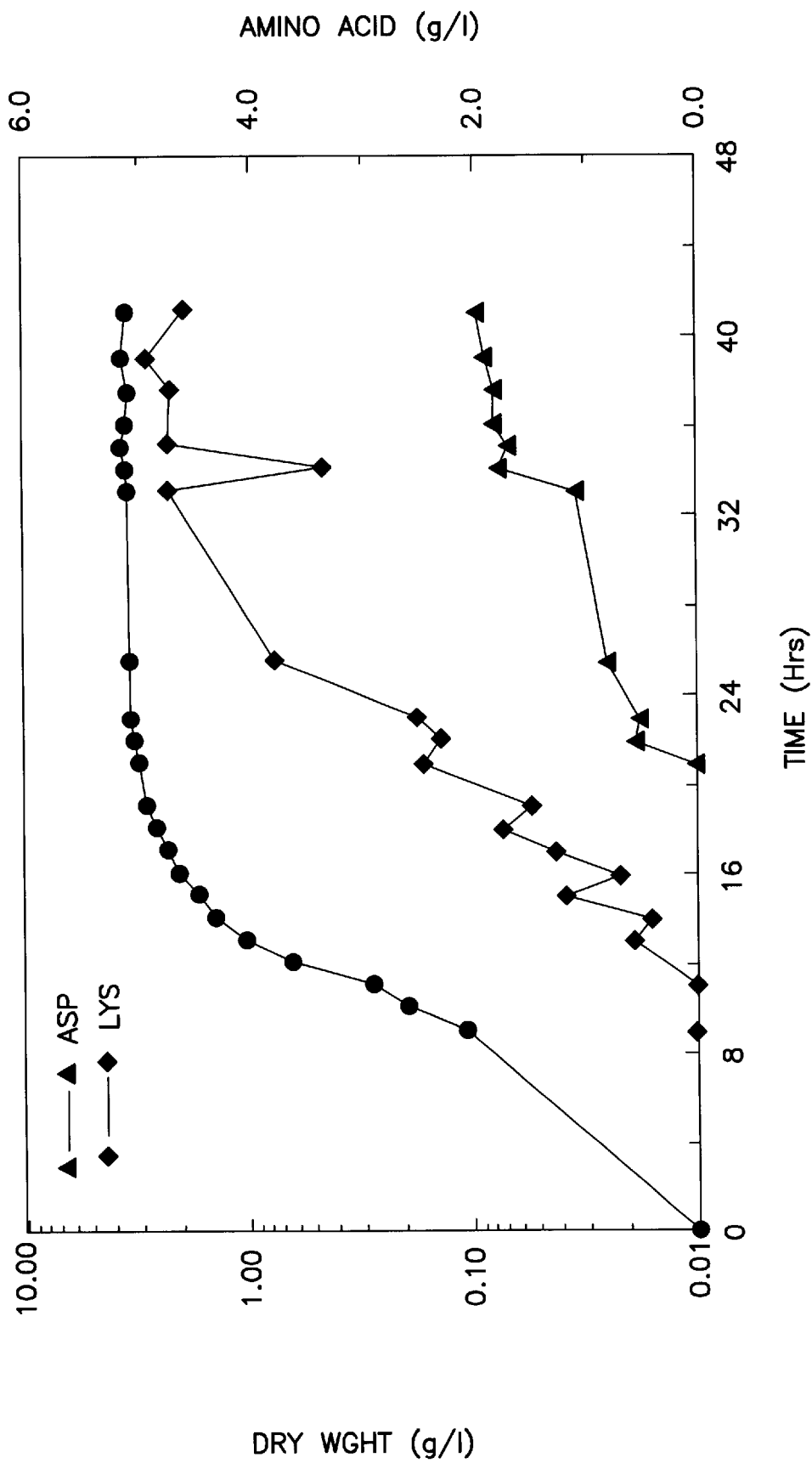
FIG. 5 shows simultaneous production of lysine and aspartic acid by an auxotrophic bacterium of the present invention.

Cultivation of the appropriate mutant using the media described in example 4, under either phosphate or sulfate limited conditions, may result in simultaneous over production of two amino acids. Using the reactor method described in example 4, the mutant NOA2 8/16-5 #3 simultaneously produced both lysine and aspartic acid. After 40 hours of cultivation, the reactor contained 3.5 g·l$^{-1}$ dry cell weight, 4.5 g·l$^{-1}$ lysine, and 2 g·l$^{-1}$ aspartic acid. (FIG. 5.)

EXAMPLE 6

A METHOD TO OBTAIN GROWTH TO HIGH CELL DENSITY

Figure 6:
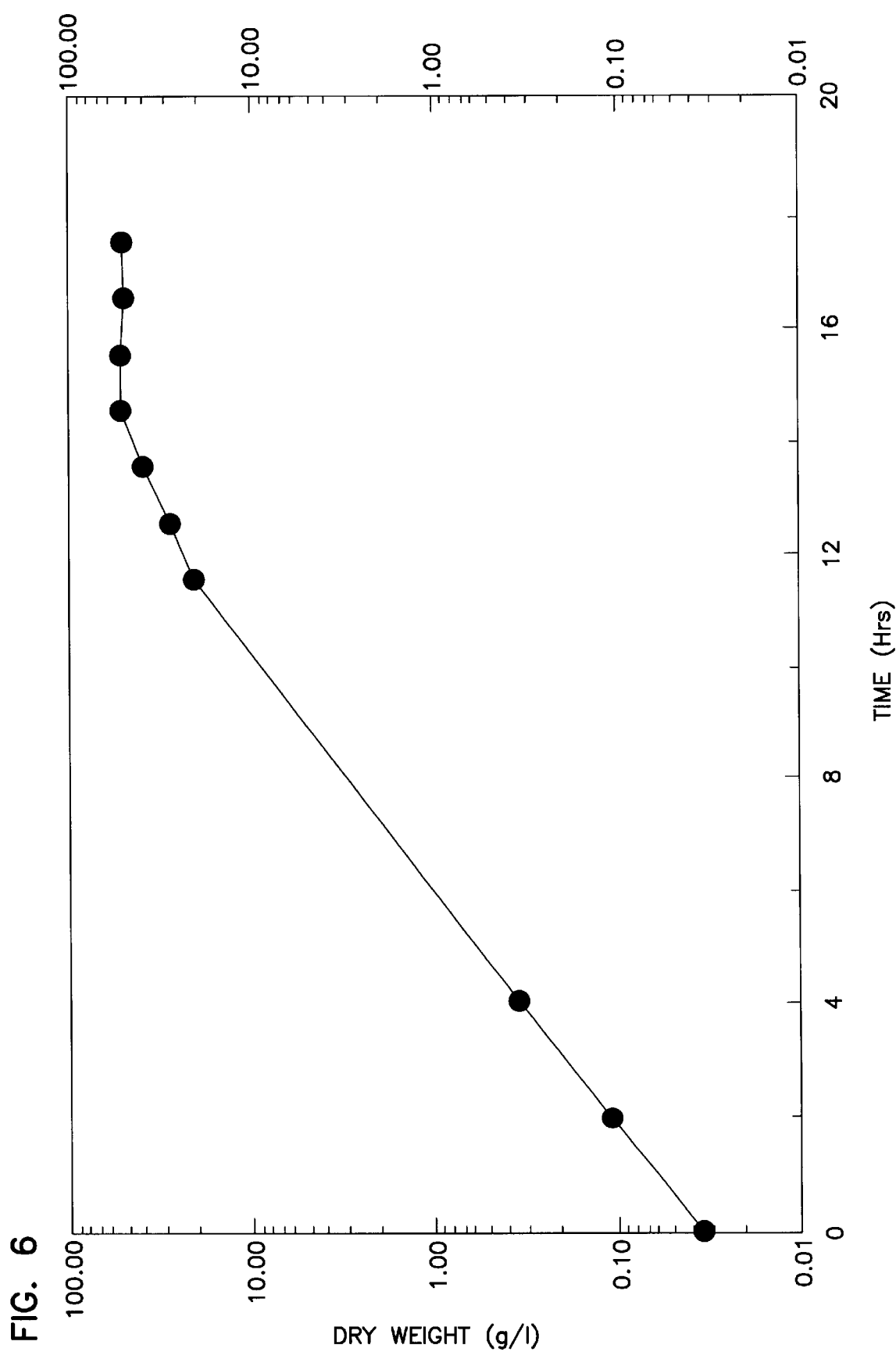
FIG. 6 shows MGA3 growth to high cell density under semi-continuous or fed-batch conditions.

The growth of MGA3 to high cell density has been accomplished by using the following medium and nutrient feeding systems. The medium contained 3.09 g·l$^{-1}$ $K_2HPO_4$, 0.9 g·l$^{-1}$ $NaH_2PO_4$, 2 g·l$^{-1}$ $(NH_4)_2SO_4$, 20 mg·l$^{-1}$ biotin, 0.2 g·l$^{-1}$ $MgCl_2.6\ H_2O$, 1 mg·l$^{-1}$ vitamin $B_{12}$, 3.98 mg·l$^{-1}$ $FeCl_2.4\ H_2O$, 7.36 mg·l$^{-1}$ $CaCl_2.2\ H_2O$, 9.9 mg·l$^{-1}$ $MnCl_2.4\ H_2O$, 136 ug/L $ZnCl_2$, 54.4 ug/L $CuCl_2.2\ H_2O$, 80.4 µg·l$^{-1}$ $CoCl_2.2\ H_2O$, 96.8 ug·l$^{-1}$ $Na_2MoO_4.2\ H_2O$, 59.6 ug·l$^{-1}$ $H_3BO_3$, 3.2 g·l$^{-1}$ methanol, and 250 mg·l$^{-1}$ yeast extract. The concentrations of the nutrients could vary as described in Example 4. Cultivation of the cells was carried out at 50° C. in a 14 liter fermentor with an 11 liter working volume. The agitation rate was varied from 900–1500 rpm. The pH was maintained at 7.1 by addition of 8N ammonium hydroxide. The ammonium hydroxide also served as a nitrogen source. Phosphate, magnesium, and calcium levels were maintained by automatically feeding a solution of 10:1:0.1 phosphate:magnesium:calcium (1M $KH_2PO_4$, 0.1M $MgCl_2.6\ H_2O$, 0.01M $CaCl_2.2\ H_2O$). Feeding of the phosphate/magnesium/calcium mix was carried our by connecting the pump to the pH controller, so that the phosphate/magnesium/calcium solution would be fed whenever the ammonium hydroxide was added to adjust the pH. The rate of the ammonium hydroxide (8N) to phosphate-magnesium-calcium feed (1M phosphate, 0.1M magnesium, 0.01 calcium) was adjusted to give a ratio of 1:2. This maintained the proper balance of nitrogen, phosphate, magnesium, and calcium. The aeration rate was varied from 0.5 to 2 vvm. The dissolved oxygen concentration was monitored by using a galvanic probe, and the level of dissolved oxygen was maintained at 30% by using pure oxygen-enriched aeration. The amount of pure oxygen used was monitored and controlled by using a mass flow controller interfaced to the dissolved oxygen probe. Foaming was controlled using a liquid level controller by the automatic addition of a silicon based anti-foam, (SAG-471). Exhaust gasses (carbon dioxide, oxygen, nitrogen, argon, methanol, ammonia, and water) were monitored by mass spectrometry. The methanol level was continuously monitored by using an on-line methanol sensor consisting of the silicon tubing probe described by Tsao, and Austin, "Control of methanol concentration using an online methanol sensor." American Chemical Society National Meeting, Toronto, Ontario, Canada (June, 1988) connected to the flame ionization detector of a gas chromatograph. The signal from the gas chromatograph was used to automatically operate the methanol feed pump. (Watson-Marlow) by use of a proportional controller. The amount of methanol fed to the culture was monitored using a load cell. The methanol also contained the required trace metals in the following concentrations: 1.09 g·l$^{-1}$ FeSO$_4$.7 H$_2$O, 0.39 g·l$^{-1}$ MnCl$_2$.4 H$_2$O, 22 mg·l$^{-1}$ ZnSO$_4$.7 H$_2$O, 19 mg·l$^{-1}$ CoCl$_2$.6 H$_2$O, 19 mg·l$^{-1}$ Na$_2$MoO$_4$.2 H$_2$O, and 19 mg·l$^{-1}$ CuSO$_4$.5 H$_2$O. Using this media and the feeding strategies described above, the organism could be grown to cell densities of 50 g·l$^{-1}$ cell dry weight (FIG. 6).

What is claimed is:

1. A biologically pure culture of a mutant of *Bacillus methanolicus*, wherein the mutant is amino acid analog resistant and capable of growth in the presence of at least about 0.25 g/L of S-aminoethyl-L-cysteine and methanol as a primary source of carbon and energy at 50° C.; and the mutant excretes at least about 5 g/L of lysine when grown in a nutrient medium comprising methanol as a primary source of carbon and energy, and ammonia or an ammonium salt.

2. The mutant of *Bacillus methanolicus* of claim 1, wherein the mutant is a mutant of *Bacillus methanolicus* strain MGA3.

3. The mutant of *Bacillus methanolicus* of claim 1, wherein the mutant is a mutant of *Bacillus methanolicus* strain NOA2.

4. The mutant of *Bacillus methanolicus* of claim 1, which further has an optimum temperature for growth in the range of 45–55° C.

5. The mutant of *Bacillus methanolicus* of claim 1, which does not grow at 65 ° C.

6. A biologically pure culture of a mutant of *Bacillus methanolicus* strain MGA3, wherein the mutant is amino acid analog resistant and capable of growth in the presence of at least about 0.25 g/L of S-aminoethyl-L-cysteine and methanol as a primary source of carbon and energy, at 50° C.; and the mutant excretes at least about 5 g/L of lysine when grown in a nutrient medium comprising methanol as a primary source of carbon and energy, and ammonia or an ammonium salt.

7. The mutant of *Bacillus methanolicus* of claim 1, which further has an optimum temperature for growth in the range of 45–55° C.

8. The mutant of *Bacillus methanolicus* of claim 6, which does not grow at 65° C.

9. A biologically pure culture of a mutant of *Bacillus methanolicus* strain NOA2, wherein the mutant is amino acid analog resistant and capable of growth in the presence of at least about 0.25 g/L of S-aminoethyl-L-cysteine and methanol as a primary source of carbon and energy, at 50° C.; and the mutant excretes at least about 5 g/L of lysine when grown in a nutrient medium comprising methanol as a primary source of carbon and energy, and ammonia or an ammonium salt.

10. The mutant of *Bacillus methanolicus* of claim 9, which further has an optimum temperature for growth in the range of 45–55° C.

11. The mutant of *Bacillus methanolicus* of claim 9, which does not grow at 65° C.

12. A mutant *Bacillus methanolicus*, wherein the mutant is capable of growth in the presence of at least about 0.25 g/L S-aminoethyl-L-cysteine; and the mutant excretes at least about 5 g/L of lysine when grown in a nutrient medium comprising methanol as a primary source of carbon and energy, and ammonia or an ammonium salt.

13. The mutant of *Bacillus methanolicus* of claim 12, wherein the mutant is a mutant of *Bacillus methanolicus* strain MGA3.

14. The mutant of *Bacillus methanolicus* of claim 12, wherein the mutant is a mutant of *Bacillus methanolicus* strain NOA2.

15. The mutant of *Bacillus methanolicus* of claim 12, which further has an optimum temperature for growth in the range of 45–55° C.

16. The mutant of *Bacillus methanolicus* of claim 12, which does not grow at 65° C.

\* \* \* \* \*

UNITED STATES PATENT AND TRADEMARK OFFICE
CERTIFICATE OF CORRECTION

PATENT NO. : 6,261,825 B1
DATED : July 17, 2001
INVENTOR(S) : Hanson et al.

It is certified that error appears in the above-identified patent and that said Letters Patent is hereby corrected as shown below:

Title page,
Item [56], References Cited, insert the following:

U.S. PATENT DOCUMENTS
-- 3,707,441    12/1972    Shiio et al. ................. 195/29

FOREIGN PATENT DOCUMENTS
0,218,130    04/1987    Europe
1,579,160    08/1969    France
57-14839    03/1957    Japan OTHER PUBLICATIONS
Linton et al., "The Potential Of One =Carbon Compounds As Fermentation Feedstocks", Source Unknown, pgs. 263-271, Dated 1985 or later
N. Al-Awadhi et al., *Appl. Microbiol. Biotechnol.*, 29, 485-493 (1988)
H. Hagino et al., *Biotech. Letters*, 3, 425-430 (1981)
Linton et al., *Microbial Growth on $C_1$ Compounds*, H. W. van Verseveld and J. A. Duine, eds., Martinus Hijhoff, Dordrecht (1987)
Large et al., *Methylotrophy and Biotechnology, Longman Scientific and Technical*, John Wiley and Sons, NewYork, NY (1988)
Holloway, *Methylotrophs: Microbiology, Biochemistry and Genetics*, C. T. Hou, ed., CRC Press, Boca Raton, FL, pp. 87-104 (1984)
Holloway et al., *Microbial Growth on $C_1$ Compounds*, H. W. van Verseveld and J. A. Duine, eds., Martinies Nyhoff, Dordrecht pp. 223-229 (1987)
Haber et al., *Science*, 221, 1147-1151 (1983)
DeVries, *FEMS Microbiol. Rev.*, 39, 235-258 (1986)
Hanson, *Biology of the Methylotrophs*, H. Dalton and C. Murrell, Eds., Marcell-Decker, pp. 1-39, (1991)
Nicholaidis and Sargent, *FEMS Microbiol. Lett.*, 41, 47-52 (1987)
Harms et al., *J. Bacteriol.*, 169, 3969-3975 (1987)
Machlin et al., *J. Bacteriol.*, 170, 141-148 (1988)
Nunn and Lidstrom, *J. Bacteriol.*. 166, 591-597 (1986)
Bohanon et al., *Appl. Environ. Microbiol.*, 54, 271-273 (1988)
DeVries, *FEMS Microbiol. Rev.*, 75, 57-102 (1990) --

Column 2,
Line 42, "lost" should read -- Most --

Column 3,
Line 45, insert after "as set forth in Table I, below." -- These methylotrophic bacteria are known as *Bacillus methanolicus*. --

UNITED STATES PATENT AND TRADEMARK OFFICE
CERTIFICATE OF CORRECTION

PATENT NO. : 6,261,825 B1
DATED : July 17, 2001
INVENTOR(S) : Hanson et al.

It is certified that error appears in the above-identified patent and that said Letters Patent is hereby corrected as shown below:

Column 6,
Line 45, "to about 0.1 $\mu$mg·1$^{-1}$" should read -- to about 0.1 mg·1$^{-1}$ --

Column 7,
Line 5, "to about/50 grams·1$^{-1}$" should read -- to about 150 grams·1$^{-1}$ --

Column 12,
Line 44, "6.5x10$^{-5}$ mMoles·min·mg$^{-1}$" should read -- 6.5x10$^{-5}$ mMoles·min$^{-1}$·mg$^{-1}$ --

Column 13,
Line 33, "ATTC No. 53908" should read -- ATCC No. 53908 --

Column 18,
Line 5, "of claim 1" should read -- of claim 6 --

Signed and Sealed this

Twenty-seventh Day of August, 2002

Attest:

JAMES E. ROGAN
Attesting Officer
Director of the United States Patent and Trademark Office